United States Patent
Bombardelli

(10) Patent No.: US 10,220,065 B2
(45) Date of Patent: Mar. 5, 2019

(54) COMPOSITIONS COMPRISING A LIPOPHILIC EXTRACT OF ZINGIBER OFFICINALE AND AN EXTRACT OF CYNARA SCOLYMUS, WHICH ARE USEFUL FOR THE PREVENTION AND TREATMENT OF OESOPHAGEAL REFLUX AND IRRITABLE BOWEL SYNDROME

(75) Inventor: Ezio Bombardelli, Groppello Cairoli (IT)

(73) Assignee: INDENA S.P.A., Milan (IT)

(*) Notice: Subject to any disclaimer, the term of this patent is extended or adjusted under 35 U.S.C. 154(b) by 1639 days.

(21) Appl. No.: 13/145,141

(22) PCT Filed: Jan. 15, 2010

(86) PCT No.: PCT/EP2010/000205
§ 371 (c)(1),
(2), (4) Date: Sep. 26, 2011

(87) PCT Pub. No.: WO2010/083968
PCT Pub. Date: Jul. 29, 2010

(65) Prior Publication Data
US 2012/0015060 A1    Jan. 19, 2012

(30) Foreign Application Priority Data

Jan. 20, 2009   (IT) .............................. MI2009A0051
Jul. 29, 2009   (IT) .............................. MI2009A1358

(51) Int. Cl.
*A61K 36/28*      (2006.01)
*A61K 36/9068*    (2006.01)

(52) U.S. Cl.
CPC .......... *A61K 36/28* (2013.01); *A61K 36/9068* (2013.01)

(58) Field of Classification Search
None
See application file for complete search history.

(56) References Cited

U.S. PATENT DOCUMENTS

2001/0046523 A1   11/2001   Newmark et al.
2008/0160116 A1   7/2008    Li et al.

FOREIGN PATENT DOCUMENTS

| DE | 198 59 499 A1 | 6/2000 |
|----|---------------|--------|
| WO | WO 99/20289 A1 * | 4/1999 |
| WO | 03/013562 A1 | 2/2003 |
| WO | 2007/006391 A2 | 1/2007 |
| WO | 2008/070783 A2 | 6/2008 |
| WO | 2008/074080 A1 | 6/2008 |
| WO | 2008/107183 A1 | 9/2008 |

OTHER PUBLICATIONS

Roy et al., Extraction of Ginger Oil with Supercritical Carbon Dioxide: Experiments and Modeling, 1996, Ind. Eng. Chem. Res., 35: 607-612.*
Phytotherapy Research: PTR Feb. 2001, vol. 15, No. 1, Feb. 2002, pp. 58-61, XP002573863; ISSN: 0951-418X.
Marakis, G. et al., "Artichoke leaf extract reduces mild dyspepsia in an open study." Phytomedicine, Gustav Fishcer Verlag, Stuttgart, vol. 9, No. 8, Jan. 1, 2002, pp. 694-699, XP00496972, ISSN: 0944-7113.
Bundy, R., et al., "Artichoke leaf extract (Cynara scolymus) reduces plasma cholesterol in otherwise healthy hypercholesterolemic adults: A randomized, double blind placebo controlled trial." Phytomedicine, Gustav Fischer Verlag, Stuttgart, vol. 15, No. 9, Sep. 3, 2008, pp. 668-675, XP023612053, ISSN: 0944-7113.
Bundy, R., et al., "Artichoke leaf extract reduces symptoms of irritable bowel syndrome and improves quality of life in otherwise healthy volunteers suffering from concomitant dyspepsia; a subset analysis" Journal of Alternative and Complementary Medicine, Mary Ann Liebert, New York, NY, US vol. 10, No. 4, Aug. 1, 2004, pp. 667-669, XP009076693, ISSN: 1075-5535.
Sailer, R. et al., "Dyspeptische Beschwerden und Phytotherapie— eine Ubersicht Uber traditionelle und moderne Phytotherapeutika [Dyspeptic pain and phytotherapy—a review of traditional and modern herbal drugs]" Forschende Komplementaermedizin-Klassische Naturheilkunderesearch in Complementary and Classical Natural Medicine, Karger, DE, vol. 8, No. 5, Oct. 1, 2001, pp. 263-273, XP008113206; ISSN: 1424-7364.
Notification of Transmittal of the International Search Report and the Written Opinion of the International Searching Authority, or the Declaration, dated Apr. 14, 2010 in Int. App. No. PCT/EP2010/000205.

* cited by examiner

Primary Examiner — Terry A McKelvey
Assistant Examiner — Catheryne Chen
(74) Attorney, Agent, or Firm — Silvia Salvadori, P.C.; Silvia Salvadori

(57) ABSTRACT

The present invention relates to compositions consisting of a combination of a lipophilic extract of *Zingiber officinale* and an extract of *Cynara scolymus*, which are useful for the prevention and treatment of oesophageal reflux and irritable bowel syndrome, to reduce postprandial drowsiness, and having prokinetic and anti-dyspeptic activities.

11 Claims, No Drawings

COMPOSITIONS COMPRISING A LIPOPHILIC EXTRACT OF ZINGIBER OFFICINALE AND AN EXTRACT OF CYNARA SCOLYMUS, WHICH ARE USEFUL FOR THE PREVENTION AND TREATMENT OF OESOPHAGEAL REFLUX AND IRRITABLE BOWEL SYNDROME

This application is a U.S. national stage of PCT/EP2010/000205 filed on Jan. 15, 2010 which claims priority to and the benefit of Italian Application No. MI2009A000051 filed on Jan. 20, 2009 and Italian Application No. MI2009A001358 filed Jul. 29, 2009, the contents of which are incorporated herein by reference.

SUMMARY OF THE INVENTION

The present invention relates to compositions consisting of a combination of a lipophilic extract of *Zingiber officinale* and an extract of *Cynara scolymus*, which are useful for the prevention and treatment of oesophageal reflux and irritable bowel syndrome, and to reduce postprandial drowsiness.

PRIOR ART

Cancer of the gastrointestinal tract is the second most common form of cancer, and the second-highest cause of death when this area is affected. Oesophagus and stomach cancer are not very common in the industrialised countries, but are extremely lethal.

A number of contributory causes have been identified for these two tumours, such as abuse of spirits, often combined with smoking, a nitrate-rich diet, and/or products or habits that break the mucus barrier in the stomach and oesophagus. Following examination of eating habits and deficiencies of some trace elements in populations from different continents (Plummer-Vinson and Paterson-Kelly syndromes), attempts have been made to prevent the onset of carcinoma of the stomach and oesophagus due to said contributory causes by modifying eating habits and lifestyles, and using medicinal or diet products. Although many of said contributory causes have been eliminated, the global incidence has increased because of an increase in the number of people suffering from gastro-oesophageal reflux, often associated with diet and/or hiatus hernia, which is one of the main causes of oesophageal tumours. Adenocarcinoma is manifested by dysplastic columnar epithelium in the distal part of the oesophagus, nearly always in the presence of chronic reflux and gastric metaplasia of the epithelium (Barrett's oesophagus), which are common in obese individuals, and becomes malignant in over 50% of cases.

It is therefore very important to reduce the incidence of this disorder.

Research is consequently oriented towards drugs able to reduce reflux, especially by modifying gastric voiding. In particular, researchers are attempting to develop well-tolerated natural prokinetics, as the potential drug will have to be taken chronically for many years on a preventive basis, or discontinuously, depending on digestive requirements.

However, many drugs which have been used recently to modify gastric voiding present serious side effects affecting the CNS or have a carcinogenic action, and have therefore either been, or are about to be, withdrawn from the market. Gastro-oesophageal reflux is currently treated with a cocktail of drugs such as proton pump inhibitors (ranitidine, -prazoles or simple antacids), enzymes, various digestive drugs, and prokinetics such as domperidone. However, long-term use of proton pump inhibitors often leads to major digestive problems.

Research is consequently now oriented towards new therapeutic approaches.

Irritable bowel syndrome affects up to 9% of the population in industrialised countries. It is a psychosomatic disorder, and is treated with antidepressants, anti-inflammatories, probiotics and other drugs, depending on its severity and duration. Irritable bowel syndrome is mainly exacerbated by stress, inadequate diet, and inflammatory states of various origins. It is also influenced by the state of the stomach. The presence of oesophageal reflux often worsens the conditions associated with irritable bowel syndrome.

DESCRIPTION OF THE INVENTION

It has now been found that a combination comprising a lipophilic extract of *Zingiber officinale*, prepared by extraction with carbon dioxide under supercritical conditions, and an extract of *Cynara scolymus*, performs a surprising prokinetic and anti-dyspeptic activity, accelerating gastric emptying, eliminating flatulence and improving the digestive function. The combination according to the invention is therefore useful for the prevention and treatment of oesophageal reflux and irritable bowel syndrome.

The present invention therefore relates to compositions containing:

a) lipophilic extract of *Zingiber officinale*, and
b) *Cynara scolymus* extract, for the increase of gastric emptying, for the prevention and treatment of oesophageal reflux, gastric voiding and irritable bowel syndrome. Moreover, the ability to increase gastric voiding significantly reduces post-prandial drowsiness, thus eliminating the problems associated with it.

More specifically, according to the invention, the lipophilic extract of *Zingiber officinale* will be prepared by extraction from the roots and rhizomes of the plant with carbon dioxide under supercritical conditions, powder being extracted from the root in an extractor at pressures of between 230 and 260 bars, preferably 235 bars, and a temperature of between 40 and 60° C., preferably 50° C., for a time ranging between 1 and 10 hours, preferably seven hours; the extract is collected in the condenser and dehydrated in inert gas dissolved in n-hexane or heptane, and concentrated under vacuum at a temperature not exceeding 40° C. Said extract contains approx. 30% gingerols, and can be used directly in the formulations according to the invention. The *Cynara scolymus* extract will be prepared by conventional methods, for example by extraction from the aerial parts of the plant with an alcohol or water-alcohol solvent and optional fractionation on resin.

The roots and rhizomes of ginger (*Zingiber officinale*), treated in various ways, are used, especially in Asia and the Middle East, as spices and in traditional medicine to treat indigestion, flatulence, diarrhoea, coughing and, to a lesser extent, to protect the mucous membranes, against inflammation, to treat urinary incontinence, etc.

The active components present in the lipophilic extract of *Zingiber officinale* mainly consist of gingerols (generally present in concentrations ranging between 10 and 15%), which possess an anti-dyspeptic, anti-nausea and anti-vomiting activity, and are useful for the treatment of motion sickness, belching, indigestion, colic, vomiting, dyspepsia and stomach and colon pain. However, recent clinical trials have demonstrated that the lipophilic extract of *Zingiber officinale* prepared by traditional methods presents low activity in view of the well-known chemical instability of gingerols; the US pharmacopoeia therefore recommends a complete review of the properties attributed to the plant due to the lack of convincing evidence. The gingerols contained in the lipophilic extract of *Zingiber officinale* prepared by traditional methods break down rapidly, giving rise to a series of compounds, such as shogaol and other products of oxidation, which are devoid of efficacy. These conflicting data are partly due to the instability of the active components in the extracts normally used. However, the extract used in the present invention is a lipophilic extract, stabilised and prepared with carbon dioxide under well-defined supercritical conditions. The *Zingiber officinale* extract accelerates gastric emptying, eliminating postprandial nausea by balancing the adverse effect of the former and completing the therapeutic effect.

Artichoke (*Cynara scolymus*) extracts are known for their choleretic, cholagogic and anti-dyspeptic action, but often cannot be used by patients suffering from irritable bowel syndrome because they worsen the alternation of constipation and diarrhoea as a result of the choleretic effect; they also slow gastric voiding and the digestive function.

The *Cynara scolymus* extracts which can be advantageously used according to the invention have a content in three classes of substances in a pre-determined ratio: caffeoylquinic acids, flavonoids derived from luteolin, and cynaropicrin. Caffeoylquinic acids exert a choleretic and liver-protecting effect, flavonoids have a blood-lipid-reducing effect associated with cholesterol synthesis, and cynaropicrin possesses an anti-inflammatory action due to interaction with nuclear factor NFκB and TNF-α.

The artichoke extract preferably contains not less than 20% caffeoylquinic acids, not less than 5% flavonoids, and not less than 5% cynaropicrin.

In the clinical field, it has surprisingly been found that the combination of these two extracts unpredictably reduces both gastro-oesophageal reflux and the intestinal parameters which are indirect contributory causes by accelerating gastric voiding, eliminating flatulence and improving the digestive function.

In patients suffering from irritable bowel syndrome with pain and dyspepsia resistant to the combination of probiotics and antidepressants, the symptoms rapidly disappeared after administration of the composition according to the invention, with a definite improvement in the quality of the life. This activity is not attributable to either of the two components taken separately.

In fact, as already stated, the choleretic, cholagogic and anti-dyspeptic action of artichoke extracts often cannot be used in patients with irritable bowel syndrome, because the choleretic effect worsens the alternation of episodes of constipation and diarrhoea, and reduces the rate of gastric voiding and the digestive function.

The present combination surprisingly improves gastric emptying and digestive function, possesses anti-dyspeptic activity and is useful for the prevention and treatment of gastro-oesophageal reflux and irritable bowel syndrome. Thus theoretically the present combination prevents the onset of oesophageal tumours.

According to a preferred aspect, the compositions according to the invention will contain the two components within the following weight intervals:

a) lipophilic extract of *Zingiber officinale*: from 1 to 25 mg; and b) extract of *Cynara scolymus*: from 50 to 200 mg.

According to a particularly preferred aspect, the compositions will contain the two components in the following quantities by weight:

a) lipophilic extract of *Zingiber officinale*: 12.5 mg; and b) extract of *Cynara scolymus*: 100 mg.

According to a preferred aspect, the lipophilic extract of *Zingiber officinale* and the *Cynara scolymus* extract will be formulated in vegetable oils rich in ω3/ω6 polyunsaturated fatty acids, such as evening primrose oil.

According to a further aspect, the compositions according to the invention may be administered together with other substances having a useful or complementary activity.

The doses which have proved active in man are 1 to 25 mg of lipophilic extract of *Zingiber officinale* and 50 to 200 mg of *Cynara scolymus* extract; more particularly, 100 mg of *Cynara scolymus* extract and 12.5 mg of *Zingiber officinale* extract per dose, to be taken with every main meal or otherwise adapted to the disorder to be treated.

The compositions according to the invention will be formulated according to conventional methods, such as those described in "Remington's Pharmaceutical Handbook", Mack Publishing Co., N.Y., USA. In particular, the compositions according to the invention will be formulated according to conventional formulation techniques for lipophilic ingredients intended for oral administration, mainly as sublingual tablets or soft gelatin or cellulose capsules for oils designed to disperse rapidly in the stomach. The lipophilic form uses oils rich in ω-3 fatty acids, which promote rapid absorption of the active ingredient, to disperse the active components. Examples of oral formulations are tablets, dragées, soft and hard gelatin capsules, and cellulose capsules.

The examples set out below further illustrate the invention.

EXAMPLE 1—EXTRACTION OF *CYNARA SCOLYMUS*

Load 1000 g of dried, minced artichoke leaves into a percolator fitted with a heating jacket, and extract 5 times with 4 L of 70% EtOH at 70° C.

Combine the filtered percolates and concentrate under vacuum to a dry residue of approx. 15%. Leave to cool at ambient temperature, then centrifuge.

Load the supernatant solution into a column packed with 1.5 L of AMBERLITE™ XAD™ 7HP resin (Rohm and Haas) previously suspended in water.

Wash the column with 1.5 L of water, then elute with 3.75 L of 90% EtOH. Concentrate the water-alcohol eluate until soft, and then dry at 50° C. under vacuum for 24 hours: 82.4 g of purified artichoke leaf extract is obtained.

HPLC titres: total caffeoylquinic acids 31.76%, total flavonoids 14.31%, cynaropicrin 17.51%.

EXAMPLE 2—SOFT GELATINE CAPSULES

Unit composition:

| | |
|---|---|
| Extract of *Cynara scolymus* | 150 mg |
| Lipophilic extract of *Zingiber officinale* | 12.5 mg |
| Glyceryl monostearate | 30 mg |
| Soya lecithin | 10 mg |
| Evening primrose oil q.s. for | 700 mg |

EXAMPLE 3—HARD GELATIN CAPSULES

Unit composition:

| Extract of *Cynara scolymus* | 100 mg |
| Lipophilic extract of *Zingiber officinale* | 12.5 mg |
| Microcrystalline cellulose | 300 mg |
| Lactose | 170 mg |
| Silicon dioxide | 5 mg |
| Magnesium stearate | 5 mg |

The invention claimed is:

1. A composition for the prevention and treatment of oesophageal reflux and irritable bowel syndrome, said composition containing two components: within the following weight ranges
 a) from 1 to 25 mg of a lipophilic extract of *Zingiber officinale* obtained by extraction with carbon dioxide under supercritical conditions; and
 b) from 50 to 200 mg of a dry extract of *Cynara scolymus* obtained by extraction with alcohol, or water-alcohol solvent, wherein the dry extract of *Cynara scolymus* contains not less than 20% of caffeoylquinic acids, not less than 5% flavonoids and not less than 5% cynaropicrin.

2. The composition as claimed in claim 1, containing the two components in the following weight amounts:
 a) lipophilic extract of *Zingiber officinale*: 12.5 mg; and
 b) dry extract of *Cynara scolymus*: 100 mg.

3. The composition as claimed in claim 1, wherein after the extraction with alcohol, or water-alcohol solvent, the extract of *Cynara scolymus* is obtained by fractionation on a resin.

4. The composition according to claim 1 formulated for oral administration.

5. The composition as claimed in claim 4 formulated in the form of soft gelatin capsules or cellulose capsules to contain oil substances.

6. A method of preventing and/or treating oesophageal reflux and irritable bowel syndrome comprising:
 administering an effective amount of a composition containing two components: within the following weight ranges
 a) from 1 to 25 mg of a lipophilic extract of *Zingiber officinale* obtained by extraction with carbon dioxide under supercritical conditions; and
 b) from 50 to 200 mg of a dry extract of *Cynara scolymus* obtained by extraction with alcohol, or water-alcohol solvent, wherein the dry extract of *Cynara scolymus* contains not less than 20% of caffeoylquinic acids, not less than 5% flavonoids and not less than 5% cynaropicrin; and
 preventing and/or treating oesophageal reflux and irritable bowel syndrome in said patients.

7. A method of reducing postprandial drowsiness comprising:
 administering an effective amount of a composition containing two components: within the following weight ranges
 a) from 1 to 25 mg of a lipophilic extract of *Zingiber officinale* obtained by extraction with carbon dioxide under supercritical conditions; and
 b) from 50 to 200 mg of a dry extract of *Cynara scolymus* obtained by extraction with alcohol, or water-alcohol solvent, wherein the dry extract of *Cynara scolymus* contains not less than 20% of caffeoylquinic acids, not less than 5% flavonoids and not less than 5% cynaropicrin to patients in need thereof; and
 reducing postprandial drowsiness in said patients.

8. A method of treating motion sickness comprising:
 administering an effective amount of a composition containing two components: within the following weight ranges
 a) from 1 to 25 mg of a lipophilic extract of *Zingiber officinale* obtained by extraction with carbon dioxide under supercritical conditions; and
 b) from 50 to 200 mg of a dry extract of *Cynara scolymus* obtained by extraction with alcohol, or water-alcohol solvent, wherein the dry extract of *Cynara scolymus* contains not less than 20% of caffeoylquinic acids, not less than 5% flavonoids and not less than 5% cynaropicrin to patients in need thereof; and
 treating said motion sickness in said patients.

9. The method of claim 6, wherein said effective amount is 12.5 mg of said lipophilic extract of *Zingiber officinale* and 100 mg of *Cynara scolymus* extract per dose.

10. The method of claim 7, wherein said effective amount is 12.5 mg of said lipophilic extract of *Zingiber officinale* and 100 mg of *Cynara scolymus* extract per dose.

11. A method of treating dyspepsia comprising:
 administering an effective amount of a composition containing two components within the following weight ranges
 a) from 1 to 25 mg of a lipophilic extract of *Zingiber officinale* obtained by extraction with carbon dioxide under supercritical conditions; and
 b) from 50 to 200 mg of a dry extract of *Cynara scolymus* obtained by extraction with alcohol, or water-alcohol solvent, wherein the dry extract of *Cynara scolymus* contains not less than 20% of caffeoylquinic acids, not less than 5% flavonoids and not less than 5% cynaropicrin to patients in need thereof; and
 treating said dyspepsia in said patients.

* * * * *